US00PP24858P2

(12) United States Plant Patent
Bergman

(10) Patent No.: US PP24,858 P2
(45) Date of Patent: Sep. 9, 2014

(54) ***CHRYSANTHEMUM* PLANT NAMED 'CIDZ0046'**

(50) Latin Name: *Chrysanthemum×morifolium*
Varietal Denomination: CIDZ0046

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 52 days.

(21) Appl. No.: 13/694,624

(22) Filed: Dec. 18, 2012

(51) Int. Cl.
*A01H 5/00* (2006.01)

(52) U.S. Cl.
USPC ..... Plt./286

(58) Field of Classification Search
USPC ..... Plt./286
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0046' particularly distinguished by single/daisy type flower form with large red and yellow bi-colored ray florets, uniform habit with strong stems, medium yellow-green foliage color, and a 7 week blackcloth flowering response time.

1 Drawing Sheet

Latin name of the genus and species of the plant claimed: *Chrysanthemum×morifolium.*
Varietal denomination: 'CIDZ0046'.

BACKGROUND OF THE NEW PLANT

The present invention comprises a new *Chrysanthemum*, botanically known as *Chrysanthemum×morifolium*, and hereinafter referred to by the variety name 'CIDZ0046'.

'CIDZ0046' is a product of a planned breeding program. The new cultivar has single/daisy type flower form with large red and yellow bi-colored ray florets, uniform habit with strong stems, medium yellow-green foliage color, and a 7 week blackcloth flowering response time.

'CIDZ0046' originates as a naturally occurring whole plant mutation of 'Yoapple Valley', U.S. Plant Pat. No. 21,420. 'CIDZ0046' was discovered and selected by the inventor as a single flowering plant within a large population of the parent cultivar, grown in pots outdoors under a shade structure in Fort Myers, Fla. in March 2009. The parent cultivar 'Yoapple Valley' has slightly larger, more red-purple, and white bi-colored inflorescences.

The first act of asexual reproduction of 'CIDZ0046' was accomplished when vegetative cuttings were propagated from the initial selection in June 2009 in a greenhouse in Fort Myers, Fla.

BRIEF SUMMARY OF INVENTION

Horticultural examination of plants grown from cuttings of the plant initiated in June 2009, and continuing thereafter, has demonstrated that the combination of characteristics as herein disclosed for 'CIDZ0046' are firmly fixed and are retained through successive generations of asexual reproduction.

'CIDZ0046' has not been observed under all possible environmental conditions. The phenotype may vary significantly with variations in environment such as temperature, light intensity, and day length.

A Plant Breeder's Right for this cultivar was applied for in Canada on Jun. 29, 2012, (12-7650). 'CIDZ0046' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical inflorescence and foliage characteristics of 'CIDZ0046' with colors being as true as possible with illustrations of this type. The photographic drawing in FIG. 1 shows 4 flowering plants of the new variety growing together in 1 container, and in FIG. 2 a close-up of a more mature inflorescence.

DETAILED BOTANICAL DESCRIPTION

Figure 1:
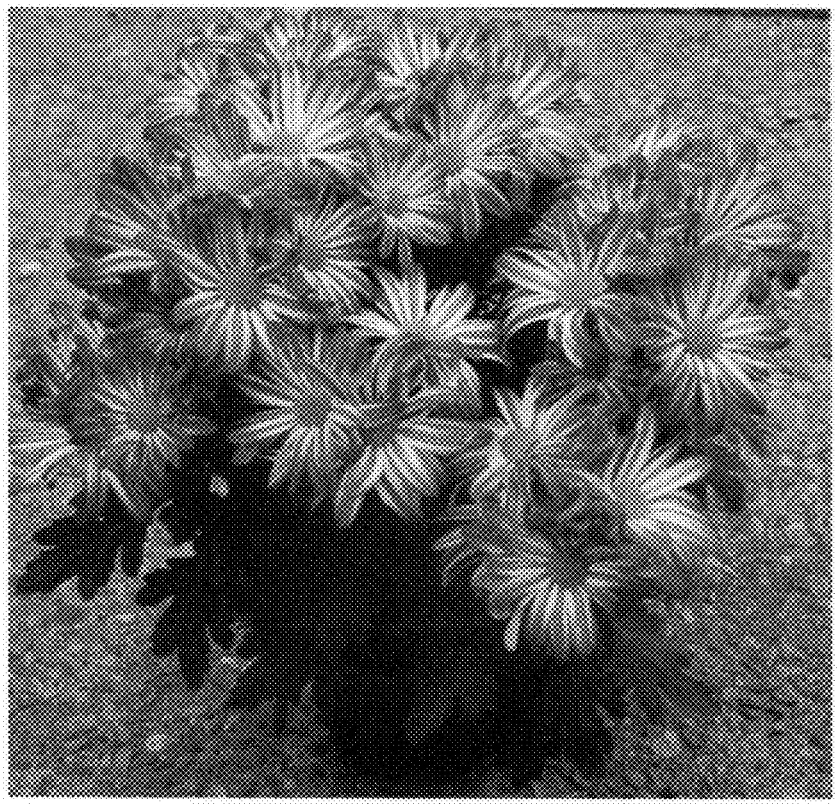
Figure 2:
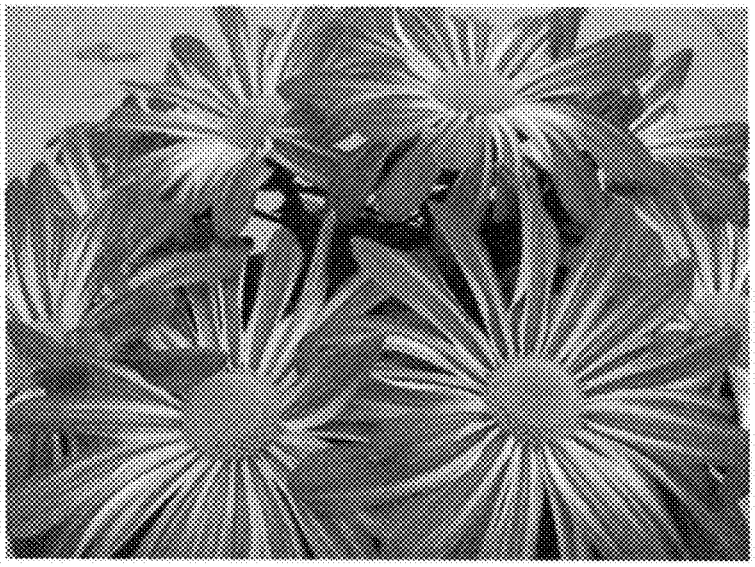

The plant descriptions, measurements and aforementioned FIG. 1 photograph were taken in Gilroy, Calif. in early October 2012 under natural light. These plants were grown 4 plants in a 6 inch container in a greenhouse in Nipomo, Calif. These plants used in the photograph and descriptions were about 10-12 weeks old. The plant for the FIG. 2 photograph was taken in Nipomo in Mid-October and was about 13-14 weeks old.

Color references are made to The Royal Horticultural Society Colour Chart (R.H.S.) 2001.

TABLE 1

DIFFERENCES BETWEEN THE NEW VARIETY 'CIDZ0046' AND A MOST SIMILAR VARIETY

| | 'CIDZ0046' | 'Yosun City' (U.S. Plant Pat. No. 17,460) |
|---|---|---|
| Inflorescence size: | Much larger | Smaller |
| Flowering response: | Faster | Slower |
| Growth habit: | Shorter, more compact | Taller, less compact |

Plant:

*Form, growth and habit*.—Herbaceous, pot-type, stems upright and freely branching, strong and moderately vigorous growth habit.

*Plant height*.—20-23.0 cm.

*Plant height* (*inflorescence included*).—25-27.0 cm.

*Plant width*.—20.0 cm.

Roots:

*Number of days to initiate roots*.—About 4 days at about 22 degrees C.

*Number of days to produce a rooted cutting*.—4-6 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 147A.

*Immature, leaf color, lower surface*.—RHS 147B with mottled spots of RHS 147C.

*Mature, leaf color, upper surface*.—Closest to but lighter than RHS 147A.

*Mature, leaf color, lower surface*.—RHS 147B but little more green with some spots of RHS 147C.

*Length*.—8.5-11.0 cm.

*Width*.—6.3-6.6 cm.

*Shape*.—Ovate.

*Base shape*.—Attenuate.

*Apex shape*.—Mucronulate.

*Margin*.—Palmately lobed; deeply incised, slightly serrate.

*Texture, upper surface*.—Bi-fid T-shaped hairs.

*Texture, lower surface*.—Bi-fid T-shaped hairs.

*Color of veins, upper surface*.—RHS 144B.

*Color of veins, lower surface*.—RHS 144B.

*Pattern of veining*.—Palmate.

*Petiole color*.—RHS 144B.

*Length*.—1.6-2.0 cm.

*Diameter*.—0.3 cm.

*Texture*.—Bi-fid T-shaped hairs.

Stem:

*Quantity of main branches per plant*.—3-4.

*Color of stem*.—RHS 138A but appears lighter due to hairs.

*Length of stem*.—17-21.0 cm.

*Diameter*.—0.4-0.5 cm.

*Length of internodes*.—0.5-1.5 cm.

*Texture of stem*.—Bi-fid T-shaped hairs.

*Color of peduncle*.—RHS 138A but appears lighter due to hairs.

*Length of peduncle*.—5.5-6.5 cm.

*Peduncle diameter*.—0.3 cm.

*Texture*.—Bi-fid T-shaped hairs.

Inflorescence:

*Type*.—Compositae, solitary, single/daisy-type inflorescences borne terminally above foliage, ray florets arranged acropetally on a capitulum.

*Quantity of short days to flowering* (*response time*).—7 weeks.

*Natural season flowering*.—Not determined on this variety.

*Quantity of inflorescences per plant*.—9-13 plus some had a few small buds.

*Lastingness of individual blooms on the plant*.—About 4-5 weeks.

*Fragrance*.—Slightly spicy.

Bud (just when opening/showing color):

*Color*.—RHS 155D to RHS 4D with a mottled hue of RHS 175A in the center of petal.

*Length*.—2.5 cm.

*Width*.—1.5 cm.

*Shape*.—Oblate.

Immature inflorescence:

*Diameter*.—6-6.5 cm.

*Color of ray florets, upper surface*.—RHS 4C to RHS 155D heavily overlaid with RHS 53A on margins and down the middle of the ray floret and more solid at the apex.

*Color of ray florets, lower surface*.—RHS 2C overlaid with closest to RHS 53C at margins and lighter shades down the middle of the ray floret.

Mature inflorescence:

*Diameter*.—10-11.7 cm.

*Depth*.—2-3.0 cm.

*Total diameter of disc*.—1.9-2.1 cm.

*Receptacle color*.—RHS 145B.

*Receptacle height*.—0.5-0.6 cm.

*Receptacle diameter*.—0.8-0.9 cm.

Ray florets:

*Average quantity of florets*.—24-33 in 2 whorls.

*Color of florets, upper surface*.—RHS 4D to RHS 155D basally becoming lighter towards the middle, overlaid mottled and slightly striated with RHS 53A becoming closest to RHS 53C more heavily in the center and margins, and more solid color toward the apex.

*Color of florets, lower surface*.—RHS 2C overlaid with closest to RHS 53D at margins and lighter shades down the middle of the ray floret.

*Length*.—4.5-5.5 cm.

*Width*.—1.2-1.4 cm.

*Shape*.—Broadly elliptical.

*Apex shape*.—Obtuse.

*Base shape*.—Cuneate.

*Margin*.—Entire.

*Texture, upper surface*.—Papillose.

*Texture, lower surface*.—Papillose.

Disc florets:

*Average quantity of florets*.—About 300.

*Color of florets*.—RHS 155C basally with RHS 3A towards the apex with RHS 145A on the very top of apex.

*Length*.—0.5 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—About 30.

*Color, upper surface*.—Closest to RHS 138A.

*Color, lower surface*.—Closest to RHS 138A.

*Length*.—0.6-0.8 cm.

*Width*.—0.15-0.30 cm.

*Shape*.—Lanceolate.

*Apex shape*.—Acute.

*Base*.—Fused.

*Margins*.—Entire, some papery.

*Texture, upper surface*.—Glabrous.

*Texture, lower surface*.—Bi-fid T-shaped hairs.

Reproductive organs:

*Pistil.*—1, found on both types of florets.

*Length.*—0.6-0.7 cm.

*Style color.*—RHS 1C.

*Style length.*—0.55-0.6 cm.

*Stigma color.*—RHS 6A.

*Stigma shape.*—Bi-parted.

*Ovary.*—Not developed enough to describe and measure.

*Stamens.*—4, found on only on the disc florets.

*Color of filaments.*—RHS 1C.

*Length filaments.*—0.2 cm.

*Anther color.*—RHS 16B.

*Anther length.*—0.2 cm.

*Anther shape.*—Oblong.

*Pollen amount.*—None observed to date.

*Fertility/seed set.*—Has not been observed to date.

*Disease/pest resistance.*—Has not been observed to date.

What is claimed is:

1. A new and distinct variety of *Chrysanthemum* plant named 'CIDZ0046' substantially as illustrated and described herein.

* * * * *